United States Patent
Reynolds et al.

(10) Patent No.: US 8,412,361 B1
(45) Date of Patent: Apr. 2, 2013

(54) REMOTE IDENTIFICATION AND VERIFICATION OF A FUNCTION PRIOR TO USE THEREOF

(76) Inventors: Charles A. Reynolds, West Haven, CT (US); Gary Argraves, Sandy Hook, CT (US)

(*) Notice: Subject to any disclaimer, the term of this patent is extended or adjusted under 35 U.S.C. 154(b) by 0 days.

(21) Appl. No.: 13/080,246

(22) Filed: Apr. 5, 2011

Related U.S. Application Data

(60) Provisional application No. 61/321,123, filed on Apr. 5, 2010.

(51) Int. Cl.
*G05B 9/02* (2006.01)

(52) U.S. Cl. .......................... 700/79; 347/3.1; 347/3.7

(58) Field of Classification Search .............. 700/79, 700/80; 340/4.1, 4.11, 4.13, 4.31, 4.34
See application file for complete search history.

(56) References Cited

U.S. PATENT DOCUMENTS

| | | | |
|---|---|---|---|
| 4,700,377 A * | 10/1987 | Yasuda et al. | 379/88.16 |
| 6,522,893 B1 * | 2/2003 | Han et al. | 455/550.1 |
| 6,600,968 B2 * | 7/2003 | Sudolcan et al. | 700/236 |
| 7,529,201 B2 * | 5/2009 | Aiken et al. | 370/278 |
| 7,792,089 B2 * | 9/2010 | Aiken et al. | 370/347 |
| 2004/0066710 A1 * | 4/2004 | Yuen et al. | 368/73 |
| 2007/0106401 A1 * | 5/2007 | Kohl et al. | 700/79 |
| 2008/0126150 A1 * | 5/2008 | Kaufman et al. | 705/7 |
| 2008/0126975 A1 * | 5/2008 | Vassigh et al. | 715/772 |
| 2010/0089728 A1 * | 4/2010 | Twellman | 200/86.5 |
| 2010/0298956 A1 * | 11/2010 | Van Eeden et al. | 700/79 |
| 2011/0012742 A1 * | 1/2011 | Johnson | 340/669 |
| 2011/0144636 A1 * | 6/2011 | Alexander et al. | 606/34 |

FOREIGN PATENT DOCUMENTS

WO  WO 2006131862 A2 * 12/2006

* cited by examiner

*Primary Examiner* — Dave Robertson

(57) ABSTRACT

Methods, systems and apparatus for enabling function identification to allow an end-user verify that a identified function is a desired function prior to activation or implementation thereof. A signal is sent from an initiating control to a receiver for identifying a particular function associated with the initiating control. An end-user is notified of this identified function and determines if the identified function is a desired function prior to activation thereof. If it is the desired function, the end-user may actuating a control associated with the initiating control to activate the function. If it is not the desired function, the end-user may stop the process or select another initiating control for repeating the process.

15 Claims, 6 Drawing Sheets

US 8,412,361 B1

REMOTE IDENTIFICATION AND VERIFICATION OF A FUNCTION PRIOR TO USE THEREOF

This application claims the benefit of U.S. Provisional Application No. 61/321,123, filed Apr. 5, 2010.

BACKGROUND OF THE INVENTION

1. Field of the Invention

This invention relates generally to end component activation control, and in particular, to identifying and verifying that a selected user control corresponds to a desired component prior to activation.

2. Description of Related Art

Various types of electronically controlled devices currently exist for enabling an end-user to actuate a user control for activation of a function (e.g., an end device). These devices either may be remotely controlled or controlled at the device itself, whereby a user control (e.g., a switch) is actuated to activate the function, such as, for example to activate an end device. After the end device has been activated, a signal is sent to the end-user for identifying the particular end device and notify the end-user that such device was activated.

However, often times the end device that has been activated is not an intended end device that was desired by the end-user. This can be detrimental in certain settings since it is often imperative that the correct device be implemented. For instance, in medical or industrial settings it is typically necessary that the correct instrument by implemented for performing a specific procedure or task so as to avoid any deleterious outcomes or end results.

As such, the notification of device activation after the device has been activated is a problem with current technologies. This impediment is further exacerbated by visual setbacks. In particular, in many situations it is often difficult for an end-user to determine whether or not they have the correct user control that activates a desired function or end device. This may be due to visual obstacles that prevent or make it difficult for the end-user to see the user control. These visual obstacles may include, but are not limited to, line-of-sight hindrances or obstacles, difficulty viewing user control identification markings, eyesight impairments, blindness, and the like.

With the various problems associated with the prior art, there continues to be a need for enabling an end-user to easily and quickly identify and verify that a selected user control corresponds to a desired function prior to activation of such function.

SUMMARY OF THE INVENTION

Bearing in mind the problems and deficiencies of the prior art, it is therefore an object of the present invention to provide systems, methods, apparatus, computer readable media, non-transitory computer readable media and/or computer program products that easily and quickly identify and verify that a selected user control corresponds to a function that is desired by the end-user prior to activation of such function.

It is another object of the present invention to provide systems, methods, apparatus, computer readable media, non-transitory computer readable media and/or computer program products for identifying and verifying that a selected user control corresponds to a desired function prior to activation thereof, whereby each and all of the same are suitable for use in industrial, commercial, residential and/or medical settings.

Still other objects and advantages of the invention will in part be obvious and will in part be apparent from the specification.

The above and other objects, which will be apparent to those skilled in the art, are achieved in the present invention which is directed to methods for function activation control that at least include initiating a first signal from a near-on initiator, identifying a function associated with the near-on initiator using the first signal, generating a second signal having the identification of the function, transmitting the second signal to a sensory component and determining if the identified function is a desired function.

In addition aspects, the invention is directed to a near-on device that at least includes a near-on initiator that initiates a first signal and has a function associated therewith, and an activating control in communication with the near-on initiator and capable of being actuated if the function associated with the near-on initiator is a desired function.

In other aspects, the invention is directed to a system for function activation control that at least includes a near-on initiator that initiates a first signal, a set of instructions that implements the first signal to identify a function associated with the near-on initiator, a second signal having the identification of the function, and a sensory component that receives the second signal for enabling determination of whether the identified function is a desired function.

In still further aspects, the invention is directed to computer readable medium, program storage devices, computer program products for function activation control that use, employ or implement the above and below described methods, apparatus and systems of the various embodiments of the invention.

The invention is also directed to methods for function activation control comprising: providing a first device in communication with a function for controlling activation of the function; temporarily actuating the first device to generate a first signal including an identification of the function prior to activation of the function; transmitting the first signal to a second device, the second device receiving the first signal and determining the identification of the function prior to activation thereof; generating a second signal having the identification of the function at the second device; transmitting the second signal to a sensory component; the sensory component alerting an end-user of the identification of the function prior to activation thereof; and verifying that the identified function that is about to be activated is a desired function prior to activation thereof, whereby, if the identified function is the desired function, then further actuating the first device to activate the function, if the identified function is not the desired function, then de-actuating the first device to prevent activation of the function.

The first device may be temporarily actuated by applying an initial pressure to the first device to generate the first signal, and if it is determined that the identified function is the desired function, the step of further actuating the first device comprises applying additional pressure to the first device thereby activating the function. The first device may be temporarily actuated by applying a constant pressure to the first device to generate the first signal, and if it is determined that the identified function is the desired function, the step of further actuating the first device comprises continuing to apply the constant pressure to the first device past a predetermined time delay associated with activation of the function thereby activating the function.

The first device may be a manually implemented device, whereby the method further includes: the end-user initially applying pressure to the manually implemented device to generate the first signal; transmitting the first signal to the second device for identification of the function; the second device receiving the first signal and determining the identification of the function prior to activation thereof; generating the second signal having the identification of the function at the second device; transmitting the second signal to the sensory component; alerting the end-user of the identification of the identified function prior to activation thereof, whereby, if the identified function about to be activated is the desired function, then the end-user continuing to apply pressure to the manually implemented device to activate the function, if the identified function is not the desired function, then the end-user ceasing applying pressure to the manually implemented device to prevent activation of the function.

The pressure may be continued to be applied to the manually implemented device by applying additional pressure to the manually implemented device thereby activating the function. The pressure may also be continued to be applied to the manually implemented device by applying constant pressure to the manually implemented device past a time delay associated with activation of the function thereby activating the function.

Wherein the manually implemented device comprises a foot-operated switch, a foot of the end-user applying the initial pressure to the foot-operated switch to generate the first signal whereby: if the identified function about to be activated is the desired function, then the foot of the end-user continuing to press down on the foot-operated switch to activate the function, or if the identified function is not the desired function, then removing the end-user's foot from contact with the foot-operated switch to prevent activation of the function.

Alternatively, the manually implemented device may be a hand-operated switch, a hand of the end-user applying the initial pressure to the hand-operated switch to generate the first signal whereby; if the identified function about to be activated is the desired function, then the hand of the end-user continuing to press down on the hand-operated switch to activate the function, or if the identified function is not the desired function, then removing the end-user's hand from contact with the hand-operated switch to prevent activation of the function.

The first device may be an electrically operated component selected from the group consisting of a mechanical switch, analog switch, electrical switch, limit switch, process switch, potentiometer, sensors, hall device and combinations thereof. The first device may be a single user control. Alternatively, the first device may be at least a two-part user control including a near-on initiator first user control in combination with an activating second user control, the near-on initiator first user control configured to be actuated before the activating second user control, whereby the near-on initiator first user control is actuating to generate the first signal, and if it is determined that the identified function is the desired function, the activating second user control is then actuated to activate the function.

Further, the first device may be actuated by human contact, electrical contact, pressure, partial pressure, rotation, sound activation, remotely and combinations thereof. The sensory component may be selected from the group consisting of a visual component, an auditory component and combinations thereof. The first signal may be remotely transmitted from the first device to the second device. The function may be a third device capable of activation selected from the group consisting of an end device, a tool, electronic equipment, a machine, an apparatus, medical equipment, and combinations thereof.

Alternatively, the function may be selected from the group consisting of a task, a sub-function, a utility and combinations thereof.

In the invention, the first signal may include a unique identifier of the first device and state information corresponding to a state of actuation of the first device, the state of actuation of the first device correlating to whether or not the function has been activated. Wherein the state information is used to determine whether at least first and second predetermined threshold values have been met, the first threshold value may be a start of a warning period at which the first device has been actuated, and the second threshold value may be an end of the warning period at which the function has been activated. The threshold values may be selected from parameters associated with user controls consisting of voltages, current, magnetic field strength, impedance, resistance, capacitance, time delays, light intensity, temperature intensity, pressure, fluid levels, particulate levels, and the like, or even in any combinations thereof.

In another aspect the invention is directed to methods for function activation control comprising: providing a manually implemented device in communication with a function for controlling activation of the function; an end-user initially actuating the manually implemented device to generate a first signal including an identification of the function prior to activation of the function; transmitting the first signal from the manually implemented device to a receiving device through a remote wireless communication, the receiving device at least determining the identification of the function prior to activation thereof; generating a second signal including the identification of the function at the second device; transmitting the second signal to a sensory component; the sensory component alerting the end-user of the identification of the function prior to activation thereof; and verifying that the identified function is a desired function prior to activation of the function, whereby, if the identified function is the desired function, then further actuating the manually implemented device to activate the function, or if the identified function is not the desired function, then de-actuating the manually implemented device to prevent activation of the function.

In these embodiments, the manually implemented device may be a foot-operated switch, a foot of the end-user applying the initial pressure to the foot-operated switch to generate the first signal whereby, if the identified function about to be activated is the desired function, then the foot of the end-user continuing to press down on the foot-operated switch to activate the function; or if the identified function is not the desired function, then removing the end-user's foot from contact with the foot-operated switch to prevent activation of the function. Alternatively, the manually implemented device may be a hand-operated switch, a hand of the end-user applying the initial pressure to the hand-operated switch to generate the first signal whereby, if the identified function about to be activated is the desired function, then the hand of the end-user continuing to press down on the hand-operated switch to activate the function; or if the identified function is not the desired function, then removing the end-user's hand from contact with the hand-operated switch to prevent activation of the function.

In the various embodiments of the invention, the function that is to be activated may be associated with a device that performs a task in a field selected from the group consisting of medical, hospital, scientific, laboratory, commercial, industrial, manufacturing and residential. This task may be performed by operation of a tool that is activated upon activation of the function.

Still other embodiments are directed to a system for function activation control comprising: a first device in communication with a function for controlling activation of the function; a first signal generated by and wirelessly transmitted from the first device, the signal including an identification of the function prior to activation of the function; a second device receiving the first signal; a set of instructions within the second device that determine the identification of the function prior to activation thereof; a second signal generated by and transmitted from the second device; a sensory component in communication with the second device, the sensory component receiving the second signal and alerting an end-user of the identification of the function prior to activation thereof for enabling determination of whether the identified function is a desired function.

The invention may further be directed to computer readable medium, program storage devices, computer program products for function activation control that use, employ or implement the above described methods, apparatus and systems of the various embodiments of the invention.

BRIEF DESCRIPTION OF THE DRAWINGS

The features of the invention believed to be novel and the elements characteristic of the invention are set forth with particularity in the appended claims. The figures are for illustration purposes only and are not drawn to scale. The invention itself, however, both as to organization and method of operation, may best be understood by reference to the detailed description which follows taken in conjunction with the accompanying drawings in which:

Figure 1:
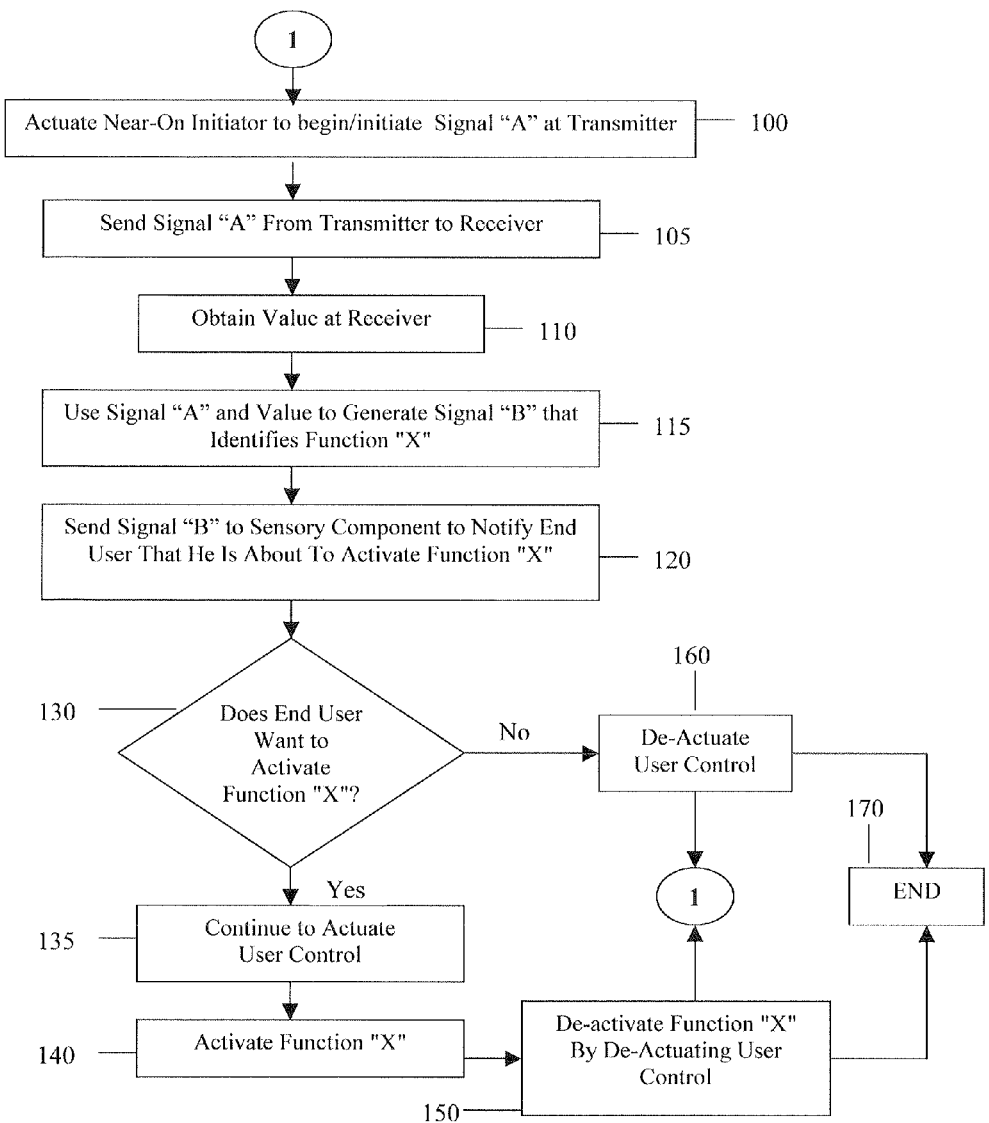
FIG. 1 is a process flow of one or more embodiments of the present invention.

DESCRIPTION OF THE PREFERRED
EMBODIMENT(S)

In describing the embodiments of the present invention, reference will be made herein to FIGS. 1A-7 of the drawings in which like numerals refer to like features of the invention.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The following embodiments were chosen and described in order to best explain the principles of the invention and the practical application, and to enable others of ordinary skill in the art to understand the invention for various embodiments with various modifications as are suited to the particular use contemplated.

The various embodiments of the invention enable function identification to allow an end-user to verify that the identified function is a desired function prior to activation or implementation of such function. That is, the invention not only indicates that something is about to happen, it also identifies the exact function(s) that is about to happen. This may be accomplished either remotely or at the end-component or device that includes the function or is the function itself. The embodiments of the invention may be implemented in systems, methods, apparatus, computer readable medium, non-transitory computer readable media, computer program products, and the like.

For purposes of the various embodiments of the invention the term "function" refers to any component or task that is, or can be, electronically activated, actuated, initiated, turned on/off, controlled, implemented, and the like. A function(s) may include, but is not limited to, an end device, a tool, electronic equipment, a machine, an apparatus, a function, a sub-function, a task, a utility, and the like. The embodiments of the invention are directed to "near-on" technology that indicates to an end-user that an identified function (or group of functions) is 'nearly-on' so that the end-user can determine whether or not such identified function is in fact a desired or intended function prior to the "on" state thereof. While not meant to be limiting, the term near-on or 'nearly-on' refers herein to a state of an identified function that indicates that such identified function is not yet activated but in fact is about to be activated. Further, the term activated is used herein to refer to the state of the identified function once it has been actuated, initiated, turned on, turned off, implemented, controlled, released, and the like.

The embodiments of the invention indicate or alert the end-user of these near-on states of the identified function(s) using a sensory component (e.g., visual, sound, etc.). In this manner, the end-user can verify that the correct function will be activated without the end-user having to look or feel for the actuator of interest. This is particularly important for medical and industrial applications where the operator must have his eyes concentrated on the work being accomplished. The "near-on" technology of the various embodiments of the invention are suitable for application in both wired and wireless technologies.

Referring to the drawings, FIG. 1 shows a first process flow suitable for use with one or more embodiments of the invention. The flowchart and block diagrams in the Figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions. The process flow of FIG. 1 is as follows:

(1) Start. The process flow continues to step 100.

Figure 2:
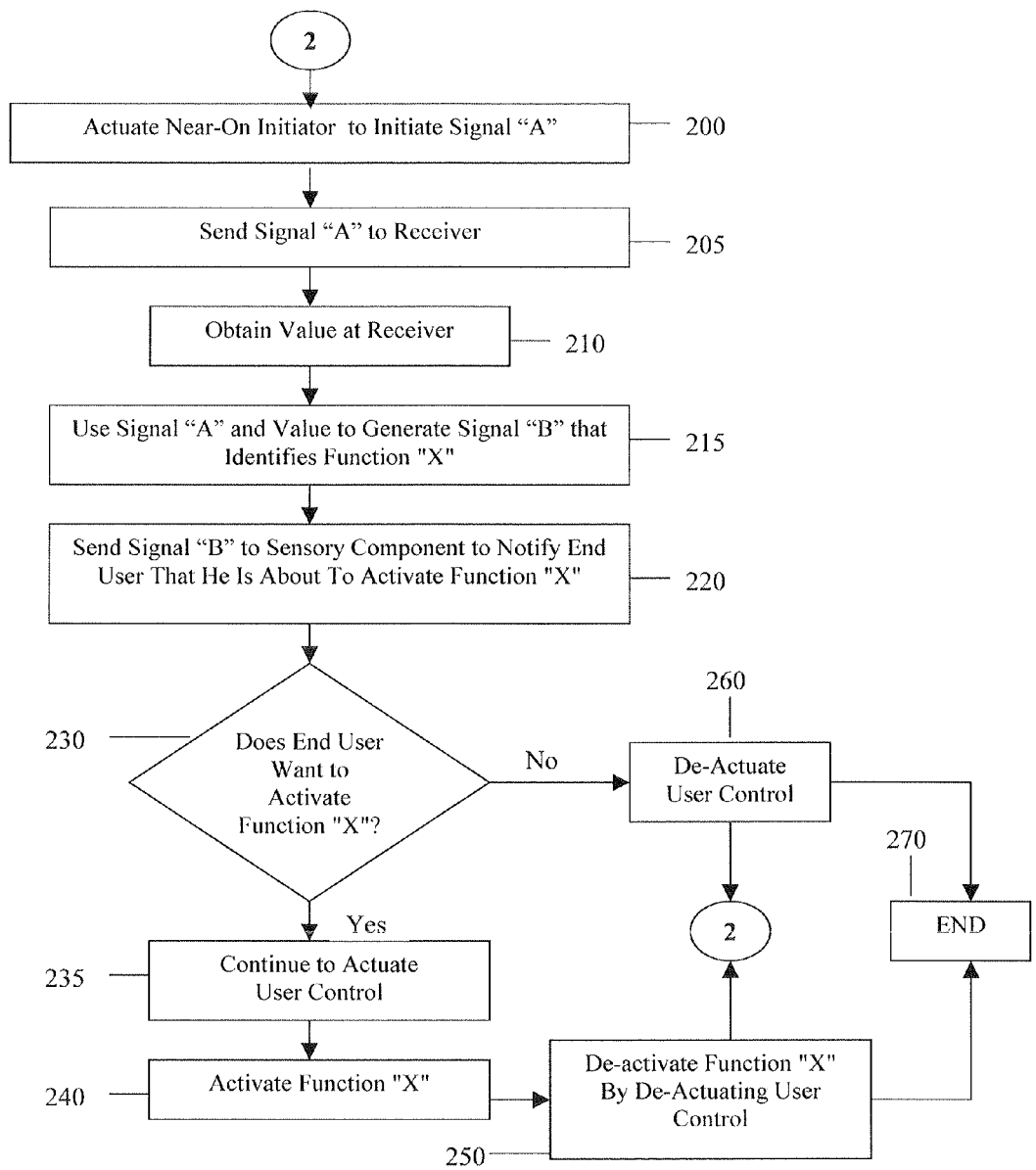
FIG. 2 is another process flow of one or more embodiments of the present invention.

100 Actuate Near-on initiator to begin/initiate Signal "A" at Transmitter. An end-user actuates or contacts a near-on initiator 416, which is discussed in more detail below, to initiate or begin a first signal (i.e., Signal "A"). The near-on initiator 416 may be located on a first device 410 that includes a transmitter 412 as shown in FIGS. 1 and 4A, or it may be on a device having a receiver as shown in FIGS. 2, 4B and 5. In the process flow of FIG. 3, the near-on initiator 416 may reside in, at or on a first device 410 that is separate from the device having a receiver, or it may reside directly in, at or on the device that includes the receiver.

The various types of user controls 414 associated with the near-on initiator 416 and suitable for use in the embodiments of the invention are discussed in detail below.

105 Send Signal "A" From Transmitter to Receiver. Once the first signal is initiated at the transmitter, the signal is sent from the transmitter to the receiver. In instances when the device having a transmitter is remote from the device having a receiver, the signal may be digitally transmitted from the transmitter to the receiver. Alternatively, when the device with the transmitter and the device with the receiver are electrically hardwired to one another, the signal may be sent via a wire transmission.

Signal "A" at least includes logic and/or data that uniquely identifies the actuated or contacted near-on initiator 416 and/or any user control 414 associated therewith, along with state information indicating a state of actuation or contact. Software or logic resides in the device having the receiver and is configured to attribute the unique identification of the near-on initiator and/or user control with a specific function or group of functions. Alternatively, signal "A" may include logic and/or data that uniquely identifies the specific function "X" or functions "X, Y, Z, AA . . . " that correspond to the actuated or contacted near-on initiator 416 and/or any user control 414 associated therewith. In these embodiments, signal "A" also includes state information relating to the state of actuation or contact of the near-on initiator and/or user control. The process flow continues to step 110.

110 Obtain Value at Receiver, and 115 Use Signal "A" and Value to Generate Signal "B" that Identifies Function "X". For ease of understanding the invention, these two steps are discussed in relation to each other below.

The receiver 422 receives the first signal for obtaining a "value" of the invention. The near-on initiator 416 may be any type of component that is capable of generating a signal that identifies either the implemented near-on initiator/user control or the specific function(s) that corresponds to the implemented near-on initiator/user control, along with state information. For instance, the near-on initiator 416 may be a single user control, a first of two or more user controls, a resistive or capacitive layer associated with a particular user control, software or logic associated with a particular user control, and the like. Since the near-on initiator may be a user control itself, or a component separate and distinct from the user control that activates function "X", the obtained value varies based on the type of near-on initiator 416 actuated or contacted by the end-user.

Various embodiments of the invention employ the use of a user control 414, which include both known user controls and user controls that are unique to the present invention. Known user controls 414 suitable for use in one or more embodiments of the invention include, but are not limited to, a foot switch, hand switch, mechanical switch, analog switch, electrical switch, limit switch, process switch, potentiometer, sensors (e.g., a temperature sensor), hall device (e.g., a linear hall sensor), and the like.

Hand switches are typically actuated by human contact. Suitable hand switches for use in the various embodiments of the invention include, but are not limited to, a toggle switch, pushbutton switch, selector switch, joystick switch, and the like. A foot switch suitable for use may be a foot operated pedal. Limit switches are specifically designed to be operated by the motion of a machine rather than by the hand of a human operator and may include, but are not limited to, a lever actuator limit switch, proximity switch, and the like. Process switches are actuated by changes in some physical process (temperature, level, flow, etc.). Suitable process switches include, but are not limited to, a speed switch, pressure switch, temperature switch, liquid level switch, liquid flow switch, and the like. The user control may further be any type of control that actuates a specific function or group of functions envisioned by and encompassed within the novel concepts of the invention.

The following paragraphs relate to embodiments of the invention wherein the near-on initiator 416 is a single user control 414, which is referred to below as a near-on control.

In one or more of these embodiments the actuated or contacted near-on control may be analog in nature, whereby measured values obtained from the near-on control are transmitted via signal "A" and compared to predetermined threshold values. The threshold values may include a start from a point or time just prior to actuating the near-on initiator, a warning period that the function "X" 430 is about to be activated, and after expiration of the warning period, an activation point or time at which function "X" 430 is activated. Alternatively, the threshold values may be limited to those values pertaining to the warning period. For instance, a first threshold value may be the start point of the warning period (e.g., a start time, start voltage, start magnetic field strength, etc.), while a second threshold value may be an end point of the warning period (e.g., a start time, start voltage, start magnetic field strength, etc.).

Figure 7:
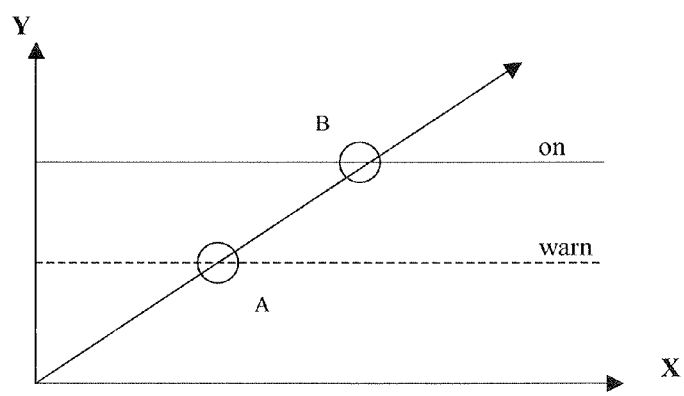
FIG. 7 is a graphical representation of measuring threshold values in accordance with various embodiments of invention.

Referring to FIG. 7, in one or more embodiments, the near-on control may be partially actuated whereby signal "A" is generated and transmitted to the receiver. For instance, a pedal, switch, sensor, etc. may be partially pressed. The signal "A" includes either an identification of the function "X" to be activated that corresponds to the actuated near-on control, or an identification of the implemented near-on control with software or logic determining the correlating function(s) to be activated. State information is also transmitted with signal "A". The state information indicates the state of actuation or contact of the near-on control, and is in a form that is dependent upon the type of near-on control actuated or contacted. For instance, state information may include, but is not limited to, a voltage measurement, an "on" indicator coupled with a time delay, a resistance measure alone or coupled with a time delay, capacitance measure alone or coupled with a time delay, and the like.

In obtaining the "value" through use of threshold values, the process starts once signal "A" is received by software or logic running on a processor of the device with receiver 422. At this point, the value obtaining process begins at the (0,0) X,Y coordinates on the graph of FIG. 7. Once signal "A" is received, if the identification of the function(s) to be activated is transmitted in signal "A" along with the identification of the actuated near-on initiator, then this information is input into the software or logic. If signal "A" does not include the identification of the function(s) that is about to be activated, then the software or logic receives the unique identification of the implemented near-on control and correlates this data with the specific function or group of functions that such implemented near-on control is set to activate. This data will be used to generate signal "B" as discussed further below.

Also transmitted within signal "B" is the threshold value data. The threshold values are measured and determined using the state information transmitted within signal "A". Again, this state information indicates the current state of the near-on control that was actuated or contacted. For instance, the current state may indicate whether or not the near-on control remains to be in an actuated or contacted position, or it may be a voltage measure that is continually measured and transmitted via signal "A" while the near-on control continues to be actuated or contacted, and the like. It should be appreciated that the state information may be measured and supplied to the processor in a variety of different parameters associated with electronic or mechanical controls including, but not limited to, voltages, current, magnetic field strength, impedance, resistance, capacitance, time delays, light intensity, temperature intensity, pressure, fluid levels, particulate levels, and the like, or even in any combinations thereof.

Regardless of the parameter of the state information, software or logic uses this state information to determine whether or not a threshold value has been met or passed. That is, the threshold value(s) may be measured in parameters including, but not limited to, voltages, current, magnetic field strength, impedance, resistance, capacitance, time delays, light intensity, temperature intensity, pressure, fluid levels, particulate levels, and the like, or even in any combinations thereof. The threshold values may include a start point/time, a warning period and an activation point/time. State information in signal "A" may be continuously received and compared against these threshold values to determine whether any transmitted state information value(s) (i.e., threshold measurements received from the near-on initiator 416) fall within or exceed any threshold value. For instance, the warning and/or activation periods may be set by time intervals, voltage levels, and the like.

Once a state value falls within one of the threshold value periods, software or logic detects this occurrence and transforms it into a signal for notifying the end-user either that an identified function is about to be activated (the start of the warning period), or that a function has been activated (the end of the warning period). As an alternative, the signal may be used to notify the end-user that the identified function is about to be turned off (the start of the warning period), or that the function has been turned off (the end of the warning period).

Signal "B" is generated in step 115 using the identification of the function(s) that the implemented near-on control is about to activate, and using the threshold value signal. In embodiments where partial pressure is applied to the near-on control, as the near-on control continues to be partially pressed, signal "A" continues to be transmitted to the receiver for providing the current state information which is used by the processor to determine the current threshold value signal. Upon the processor receiving the information necessary for generating signal "B", this signal "B" is sent to a sensory component to indicate to the end-user that something is about to happen (e.g., that a function(s) is about to be activated (step 120 discussed below).

As will be discussed further below, signal "B" is received at the sensory component and transmitted to the end-user once the threshold value signal within signal "B" reaches the beginning of the warning period threshold value range. During this period/time, the end-user is notified via signal "B" of the identified function "X" 430 or functions "X, Y, Z, AA . . . " 430 that is/are about to be activated. The end-user must then decide whether or not the identified function "X" or functions "X, Y, Z, AA . . . " is/are the function(s) that the end-user desires (step 130). If so, the end-user may fully actuate the near-on control (e.g., fully press a pedal) to activate such function(s) (steps 135, etc.). On the other hand, if the identified function(s) is not the desired function(s), then the end-user removes actuation from the near-on control (e.g., removes pressure from the pedal) (step 160) and the process ends (step 170).

For instance, referring to FIG. 7, the warning period may range from point A to point B, whereby once the state information value is equivalent to point A the end-user will receive the identification of the function(s) about to be activated via signal "B". The end-user is allowed to decide within this warning period range (i.e., from points A to B) whether or not the end-user wants to activate the identification function(s). Once the state information value is the same as point B, the function(s) is activated.

As alternative embodiments to partial actuation of the near-on control and holding this partial actuation state as discussed above, the end-user may either partially or fully actuate the near-on control (e.g., either partially or fully press a pedal) in a first control actuation step to initiate signal "A" followed by de-actuating the near-on control. Signal "A" is sent to the receiver for identifying the specific function(s) that is about to be activated in association with the near-on control that was actuated in the first control actuation step. Signal "A" is also sent to the receiver for starting the above state information threshold value determination process. With the near-on control in a de-actuated mode, signal "B" is generated to include the identification of the function that is about to be activated along with the threshold value signal, and is sent to a sensory component for notifying the end-user.

In these embodiments the threshold values may be measured and determined using a time delay parameter, or alternatively, any other parameter that does not require a continuous transmission of the signal "A" from the near-on control. Time delay threshold value determinations may be implemented using time delay logic. During the warning period (e.g., from time A to time B) the end-user must decide whether or not the function(s) that is about to be activated is in fact the function(s) desired by the end-user. If so, the function(s) will be activated at time B after the expiration of the warning period. The desired function(s) may be activated by fully actuating the same near-on control (e.g., fully pressing the pedal) in a second control actuation step to activate such function(s). If the function(s) is not a desired function(s), this near-on control is not actuated in a second control actuation step.

As an example of these embodiments, the near-on control may be a potentiometer whereby as the potentiometer is rotated, an initial voltage output is sent via signal "A" to the receiver. As the potentiometer is rotated a voltage output is sent via signal "A" that is proportional to the rotation. Software or logic extrapolates the signal data and indicates when a first voltage output from the potentiometer reaches the beginning of the threshold warning period. At this point, signal "B" is generated and sent to the sensory component to indicate to the end-user that the function identified within signal "B" is about to be activated. During this process signal "A" may continue to be sent to the receiver and signal "B" continuously sent to the sensory component. Once the user is notified that a certain function is about to be activated, a decision must be made whether the specific function that is associated with the potentiometer and identified in signal "B" is in fact a desired function. If the identified function is the desired function, the potentiometer continues to be rotated until a second voltage output is reached and measured. This second voltage matches the ending point of the threshold warning period, at which point, the identified function is activated. In the event the identified function is not a desired function, the rotation of the potentiometer stops.

In other embodiments of the invention, the near-on initiator 416 may be a first of two or more user controls. The following paragraphs relate to embodiments of the invention wherein the near-on initiator 416 is a first of two or more user controls.

Referring to FIGS. 4A-6, the near-on initiator 416 may be a first user control while activating user control 414 is a second user control. Together, user control 414 in combination with near-on initiator 416 form a near-on device 418 in accordance with various embodiments of the invention. In these embodiments, the first user control (i.e., the near-on initiator 416) is set in a position, location, sequence, and the like, to be actuated before the second user control is actuated (i.e., user control 414). It should be appreciated that actuation of the first user control may be accomplished by contact, pressure, partial pressure, rotation, sound activation, and the like. Also, the contact, pressure and/or partial pressure may be implemented either by the end-user or by a triggering component (e.g., liquid contacting the near-on initiator, particulate matter pressing against the near-on initiator, etc.).

Upon actuation of this first user control, signal "A" is initiated and sent to the device having receiver 422. Signal "A" may be digital in nature, and as such, transmit a one-time signal to the receiver, or it may be linear in nature and submits a continuous analog signal to the receiver. Like the above embodiments, signal "A" includes either an identification of the function "X" to be activated that is associated with the actuated first user control, or an identification of the actuated first user control with software or logic determining the function(s) to be activated correlating to the actuated first control and/or entire near-on device 418. State information indicating a state of actuation of the near-on initiator 416 is also transmitted via signal "A".

Signal "A" is sent to a processor running on a computing device, whereby software or logic of the processor obtains or determines the identification of the function or functions that is/are about to be activated. The software or logic also extrapolates the state of the near-on initiator 416. Again, the state information will vary depending on the type of user control(s) used as the near-on initiator 416. For instance, the state information may include an indication that a particular near-on initiator 416 has been actuated prior to actuating the second user control 414.

The software or logic also may use this state information from signal "A" to obtain threshold value data by determining whether or not a predetermined threshold value has been met or passed. For instance, the threshold value data may be evaluated in time delay logic parameters including a start time, a warning period and an activation time. In such embodiments, receipt of the state information parameter, which indicates that the near-on initiator 416 has been actuated, begins the start time for timing when the warning period threshold value range begins (e.g., point A in FIG. 7) and when it has been exceeded (e.g., point B in FIG. 7), at which point in time the identified function(s) will be activated.

The identification of the function(s) that is about to be activated is transmitted via signal "B" to a sensory component for use by the end-user (step 120 discussed below). The threshold value may also be transmitted in signal "B" in situations where a continuous signal "A" is received from the actuated first user control, or the software or logic running on the processor may monitor the threshold value data and signal when the actuated first user control is a digital in natures (e.g., an on/off switch or signal).

Signal "B" is sent to a sensory component whereby the end-user, or triggering component, is notified of the function(s) that is about to be activated, which starts the running of the warning period threshold value range. It must then be decided whether or not the identified function(s) is an intended or desired function(s) (step 130), and if so, the second user control 414 is actuated, either partially or fully, to activate such function(s) (steps 135, etc.). If it is not the desired function(s), then the process ends (step 170).

While not meant to limit the invention, the following are examples of near-on devices 418 in accordance with various embodiments.

In various embodiments of the invention, the near-on initiator 416 is a first user control that may be a linear input device (e.g., a potentiometer, hall device, etc.) in combination with the second user control 414 which may be a digital output device (e.g. a relay). Together, the linear input device in combination with the output device form a near-on device 418 that emulates a mechanical switch for alerting an end-user, or triggering component, that a particular function(s) is about to be activated (i.e., before the function is activated). While the foregoing is described in relation to the first user control being a linear input device and the second user control being a digital output device, it should be appreciated that these user controls may be switched such that the first user control is digital in nature and the second user control is linear in nature.

In one or more embodiments, the first linear input device is actuated to initiate a voltage output signal "A" of the linear device. This linear signal "A" is sent to the receiver for indicating that the particular actuated first linear input device was in fact actuated. The function(s) associated with this first linear input device is obtained as described above, and the threshold value determination process begins. The voltage output of the linear device may be ignored (i.e., gated off) as the purpose of the linear input control is to initiate the warning or alerting processes. In so doing, time delay threshold values may be used to determine when the warning period begins (e.g., point A), and whether or not such warning period has expired (e.g., point B). Alternatively, the voltage outputs of the linear device may be continuous measured and used for the threshold value determinations, whereby the warning period range may be set with threshold values being predetermined voltage measures that must be met or exceeded.

After the threshold "on" value has been reached, the second user control 414 which may be a digital output device (e.g. a relay) is actuated. In so doing, a hysteresis can be applied to the ON/OFF threshold levels so that the "on" threshold value is greater than the "off" threshold value. In this manner, the switched digital output device is prevented from altering between "on" and "off" states in the event the first linear input control resides at the "on" threshold level.

Signal "B" is generated to include an identification of the function(s) that is about to be activated, along with any threshold value data that may be necessary to implement the second user control. This signal "B" is sent to a sensory component for notification of the function(s) that is about to be activated, which starts the running of the warning period threshold value range. A decision is then made as to whether or not the identified function(s) is an intended or desired function(s) (step 130), and if so, the second user control 414 is actuated, either partially or fully, to activate such function(s) (steps 135, etc.). If it is not the desired function(s), then the process ends (step 170).

In other embodiments, the first and second user controls may be two digital input controls with one set to activate before the other. For instance, each of the first and second user controls may include, but are not limited to, a hall device, a digital switch, and the like. Also, the first and second user controls may be any combination of these digital controls (e.g., a digital hall in combination with a digital switch, etc.). As an alternative to two digital user controls, the user controls may be two mechanical analog user controls. In this aspect, each of the first and second mechanical analog user controls may include, but are not limited to, a linear hall device and the like, or even any combinations thereof.

Whether the first and second user controls are two digital input controls or two mechanical analog user controls, the first user control 416, which is the near-on initiator, is set in a position, location, sequence, and the like, to be actuated before the second user control 414 is actuated. Together, the first user control 416 (working as the near-on initiator) with the second user control 414 form the present near-on devices 418. It should be appreciated that actuation of the first user control may be accomplished by contact, pressure, partial pressure, rotation, sound activation, and the like. Also, the contact, pressure and/or partial pressure may be implemented either by the end-user or by a triggering component (e.g., liquid contacting the near-on initiator 416, particulate matter pressing against the near-on initiator 416, etc.).

Upon actuation of the first user control 416 (i.e., the near-on initiator), signal "A" is generated and transmitted to receiver 422. Software or logic extrapolates or determines the function(s) that is/are about to be activated in association with this first user control 416 and uses this information to generate signal "B". The threshold values and/or ranges may also be included within this signal or remain at the processor end for determining when the warning range has been met and exceeded. In some embodiments, the end-user may determine when the warning range expires upon the end-user physically actuating, or not actuating, the second digital input user control 414 at a certain point in time.

The generated signal "B" is then sent to a sensory component for notification of the function(s) that is about to be activated, which starts the running of the warning period threshold value range. A decision is then made as to whether or not the identified function(s) is an intended or desired function(s) (step 130), and if so, the second user control 414 is actuated, either partially or fully, to activate such function(s) (steps 135, etc.). If it is not the desired function(s), then the process ends (step 170).

Figure 6:
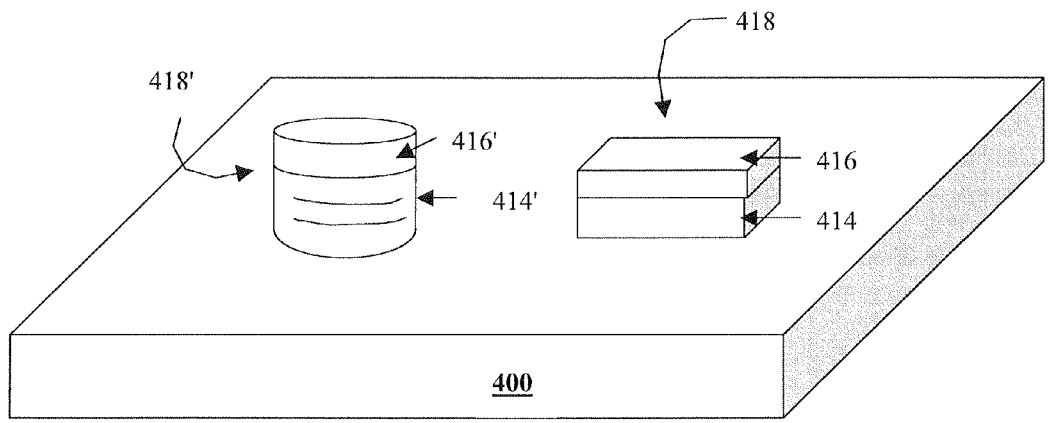
FIG. 6 is a perspective view illustrating different near-on devices in accordance with one or more embodiments of the invention.

For illustration and understanding purposes only, FIG. 6 shows two examples of near-on devices 418, 418' in accordance with various embodiments of the invention. For instance, the near-on devices 418 may include two like or similar user controls, such as, a first hall device 416 and a second hall device 414. Upon actuating the first user control hall device a magnet is pushed down onto or slides over a surface of the second user control hall device. The first user control hall device may be at a first sensitivity while the second user control hall device is at a different second sensitivity. This first sensitivity may be used as the start value of the threshold value warning range, and the second sensitivity may be used as the ending value of the threshold value warning range. The end-user is warned that a specific function associated with the first user control hall device, the second user control hall device, or both (i.e., the near-on devices 418) is about to be activated at the detection of this first sensitivity, and if the end-user wants such function to be activated, the second user control hall device having the second sensitivity is allowed to be actuated at which point the function is activated. If not, the process ends.

FIG. 6 shows another example of near-on devices in accordance with various embodiments of the invention whereby the near-on devices 418' includes two dissimilar user controls. For instance, the first user control 416' may be digital in nature while the second user control 414' is analog in nature, or vice versa. Upon actuating the first user control 416' (e.g., by contacting or applying pressure to a digital control) the initial signal "A" is sent to the receiver, and signal "B" is generated and sent to the sensory component notifying the end-user or triggering component that a specific function is about to happen or be activated, as discussed above. A determination is made as to whether or not the specific function is in fact a desired function, and if so the second user control 414' is actuated to activate the function (e.g., by rotating a potentiometer that may be associated with or in contact with the first user control 416').

It should be appreciated that more than two user controls may be implemented in any of the above described embodiments. In doing so, at least one or more user controls is/are used as the near-on initiator user control 416 and one or more user controls is/are used as the second user control 414 that activates a particular function associated therewith. For instance, a single near-on initiator user control 416 may be used in connection with two or more activation user controls 414 for providing warnings that functions associated with these two or more user controls 414 are about to be activated. Together, these one or more near-on initiator user controls 416 in combination with the one or more activation user controls 414 form the various near-on devices 418, 418' of the invention.

Figure 5A:
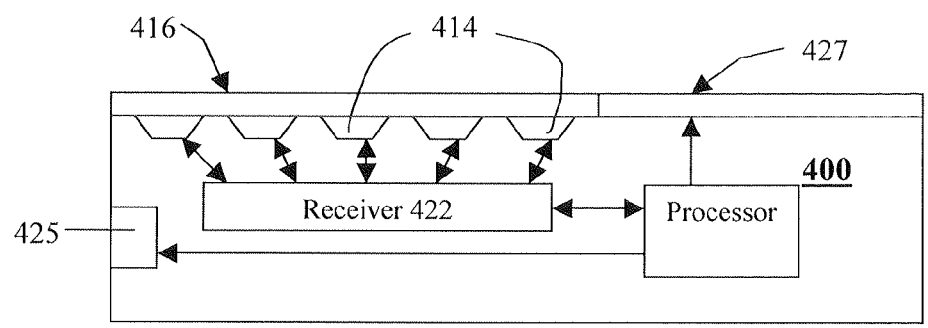
FIGS. 5A-C are cross sectional views illustrating alternate systems and apparatus of various embodiments of invention.
Figure 5B:
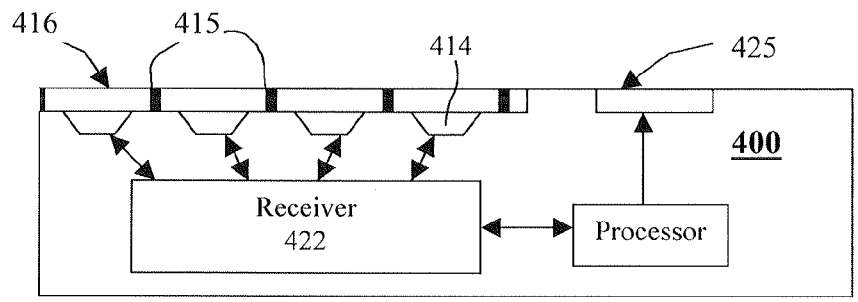
Figure 5C:
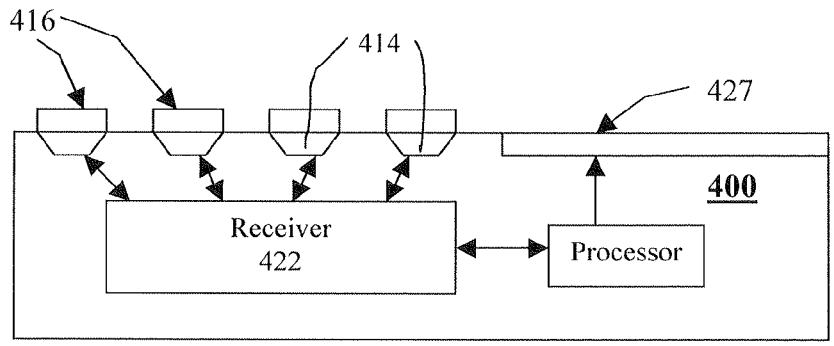

Referring to FIGS. 5A-C, in various other embodiments of the invention, the near-on initiator 416 may be a membrane or layer positioned, located or residing over or in direct contact with a user control 414. This near-on initiator membrane 416 or near-on initiator layer 416 that allows for initiating signal "A" that is sent to the receiver to start the threshold value determination process for determining whether a function associated with the membrane or layer is in fact a desired function prior to activating such function. The near-on initiator membrane or near-on initiator layer 416 is set to actuate before its corresponding user control 414 that the membrane or layer is associated therewith. In these embodiments, the near-on initiator membrane/layer 416 may be a touch sensitive, pressure sensitive user or near-contact sensitive user control, while the activating user control 414 may likewise be a touch sensitive or pressure sensitive user control, or even combinations thereof.

The near-on initiator membrane or layer 416 may reside over a plurality of user controls 414 as a single continuous layer (FIG. 5A). Alternatively, the near-on initiator membrane or layer 416 may reside over the user controls and include electrical isolation regions 415 for electrically isolating sections of the near-on initiator membrane or layer over respective user controls 414 (FIG. 5B). As another alternative, each user control 414 may have its own corresponding near-on initiator membrane or layer 416 (FIG. 5C). FIG. 2 shows an exemplary process flow for implementing these embodiments of the invention, whereby it is not necessary that a transmitter device be implemented, but rather the present near-on initiator membrane/layer over a user control of various embodiments of the invention.

In one or more embodiments the near-on initiator membrane or layer 416 may be a touch sensitive resistive membrane or layer that resides over a plurality of user controls or a single user control, which may be touch sensitive, pressure sensitive or combinations thereof. In embodiments having the resistive layer over a plurality of user controls, the resistive layer may be actuated or contacted by the end-user (e.g., the end-user physically touches or contacts the resistive layer either by hand/finger or using a touch pen, etc.). This resistive membrane or layer is coupled to the receiver. Upon contact, signal "A" is initiated and sent to the receiver whereby a processor then extrapolates data from the signal including data relating to the site of contact or actuation. The processor uses this data to determine the approximate or exact X,Y coordinate location of the site of actuation or contact on the resistive layer. This site of actuation or contact is then correlated with a specific user control 414 residing under, near or adjacent thereto, as well as with the function(s) associated with this identified specific user control 414. Together, the touch sensitive near-on resistive indicator membrane or layer 416 combined with this identified specific user control 414 (e.g., a forms a near-on device 418 of the invention.

In embodiments where the resistive membrane or layer includes electrical isolation regions 415 (FIG. 5B), each specific section of the resistive layer 416 may be coupled to the receiver for determining the site of actuation or contact along with the corresponding user control 414 residing under, near or adjacent thereto. Wherein separate, distinct regions of resistive membrane or layer reside over individual user controls 414 (FIG. 5C), each of these regions of resistive layer 416 also may be coupled to the receiver for determining the site of actuation or contact along with the corresponding user control 414 residing under, near or adjacent thereto.

Alternative to a resistive membrane or layer, the near-on initiator membrane or layer 416 may be a capacitive membrane or layer 416 residing over a plurality of user controls 414 (FIG. 5A) or a single user control 414 (FIGS. 5B-C), which may be touch sensitive, pressure sensitive or combinations thereof. This near-on capacitive indicating membrane or layer may be capacitance sensitive either by contact therewith, or by detection of a change in capacitance near or adjacent such capacitive membrane or layer (i.e., non-contact that is close enough to the capacitive membrane or layer such that it detects a change in capacitance).

Whether the change in capacitance is detected by contact or near-contact with the near-on capacitive indicating membrane or layer, a change in capacitance is detected whereby signal "A" is initiated and sent to the receiver 422. A processor running software determines the approximate or exact X,Y coordinate location of the site of actuation or contact of the capacitive membrane or layer 416. This site is then correlated with a specific user control 414 residing under, near or adjacent thereto, and identifies the function(s) associated with this identified specific user control 414. Together, the near-on capacitive indicator membrane or layer 416 combined with this identified specific user control 414 forms a near-on device 418 of the invention. This near-on capacitive indicator membrane or layer 416 may include electrical isolation regions 415 (FIG. 5B) or be separate, distinct sections of capacitive membrane or layer reside over individual user controls 414 (FIG. 5C), such that, each section of capacitive layer may be coupled to the receiver for making the necessary determinations.

Whether the near-on initiator membrane or layer 416 is resistive or capacitive, upon actuation thereof, signal "A" is generated and transmitted to receiver 422. Software or logic of a processor determines the specific user control 414 associated with the site of actuation, as well as the function(s) that is/are about to be activated in association with this identified user control 414. Signal "B" is generated to include an identification of the function(s) that is about to be activated in association with the identified user control 414, along with any threshold value data that may be necessary to implement such identified user control. Preferably, the threshold value ranges are measured in time delay parameters that identify the beginning and ending of the threshold warning period ranges, whereby the processor determines when the warning range has been met, and possibly when it has been exceeded. Again, in some embodiments the end-user may determine when the warning range expires by the end-user physically actuating, or not actuating, the identified user control 414.

Signal "B" is sent from the processor to a sensory component for notification of the function(s) that is about to be activated, which starts the running of the warning period threshold value range. A decision is then made as to whether or not the identified function(s) is an intended or desired function(s) (step 130), and if so, the user control 414 is actuated (e.g., partially of fully pressed) to activate such function(s) (steps 135, etc.). If it is not the desired function(s), then the process ends (step 170).

Whether the near-on initiator membrane or layer 416 is resistive or capacitive, signal "A" may be actuated by contact, pressure, partial pressure, near-contact, and the like, which may be maintained until the intended function is activated or further depression applied thereto to actuate the pressure or touch sensitive user control 414 for activating the identified function "X". Alternatively, a two-step contact or pressure process may be implemented, whereby the touch sensitive near-on initiator membrane or layer 416 is contacted or pressure applied thereto in a first step to generating signal "A", followed by removal of such contact/pressure. Once it is determined that the function that is about to be activated is in fact a desired function, the end-user may contact or apply pressure to the touch sensitive near-on initiator for a second time, or even apply a double pressure at this point to actuate the user control 414 that activates function "X".

120 Send Signal "B" to Sensory Component to Notify End User that He Is About to Activate Function "X". As discussed above, once signal "B" is generated, it is sent to a sensory component for notifying an end-user or a triggering component that the identified function(s) is/are about to happen or be activated. The sensory component may reside on or within an end device 400 that is the function "X" to be activated (e.g., FIGS. 5A-C), or the end device 420 may include function "X" that is to be activated (FIG. 4A), or even the sensory component may be separate and distinct from an end device (FIG. 4B).

In embodiments where the sensory component is sent to notify an end-user, these sensory components may include any type sensory alert component including, but not limited to, a visual alert 427, an auditory alert 425, and the like. Visual displays may include, but are not limited to, a visual display screen (e.g., an LCD screen), an alpha numeric display, light emitting diodes, and the like. Auditory alerts 425 may include, but are not limited to, audio voice enunciation, beeper/buzzer alerts, an audio ear piece, and the like. These sensory alerts of the 'near-on' condition may be indicated once or a plurality of times during the threshold warning period (e.g., function "X" will activate in 20 seconds, function "X" will activate in 10 seconds, . . . function "X" activated; or, function "X" 25% activated, function "X" 50% activated, . . . function "X" 100% activated; and the like). Alternatively, the sensory alerts of the 'near-on' condition may be indicated continuously during the entire threshold warning period.

In embodiments where the sensory component is sent to a triggering component the sensory component may include, but is not limited to, a light sensor, a temperature sensor, and the like. Once the sensory alert is sent and received by the end-user or triggering component, the process flow continues to step 130.

130 Does End-User Want to Activate Function "X"? Once the end-user senses the notification that the returned signal "B" is associated with a particular function "X", the end-user must determine whether or not this function "X" is the particular function that the end-user desires. Alternatively, wherein signal "B" is sent to a triggering component, then system software or logic may determine whether or not the identified function "X" is in fact a desired function. If the identified function "X" is the desired function, then the process continues to step 135. If it is not the desired function, then the process continues to step 160.

135 Continue to Actuate User Control. Once it is determined that the identified function "X" is in fact a desired function, the near-on initiator may continued to be actuated, or fully actuated, in embodiments having a single user control as the indicating near-on initiator and the activating user control. Alternatively, in those embodiments having a first near-on initiator user control, membrane or layer, in combination with a second activating user control, this second activating user control is actuated as discussed in detail above. The process continues to step 160

140 Activate Function "X". After or upon actuation of the activating user control 414, the identified function "X" is activated. This activation will continue for a predetermined time, or until the end-user decides to stop the process. Continue to step 150.

150 De-activate Function "X" by De-actuating User Control. Once the end-user no longer wants to activate function "X", actuation of the activating user control stops. For instance, applied pressure,

160 De-actuating User Control. Once it is determined that the identified function "X" is not a desired function, the near-on initiator 416 is de-actuated and the process ends at step 170.

170 End. The process may end by de-actuating a near-on initiator 416 that correlates with either a desired or undesired function. Alternatively, the process may ended when the near-on initiator 416 has been de-actuating due to a lack of a signal. Once the process ends, it may be repeated at step (1) for a new near-on initiator or a previously actuated near-on initiator.

Figure 3:
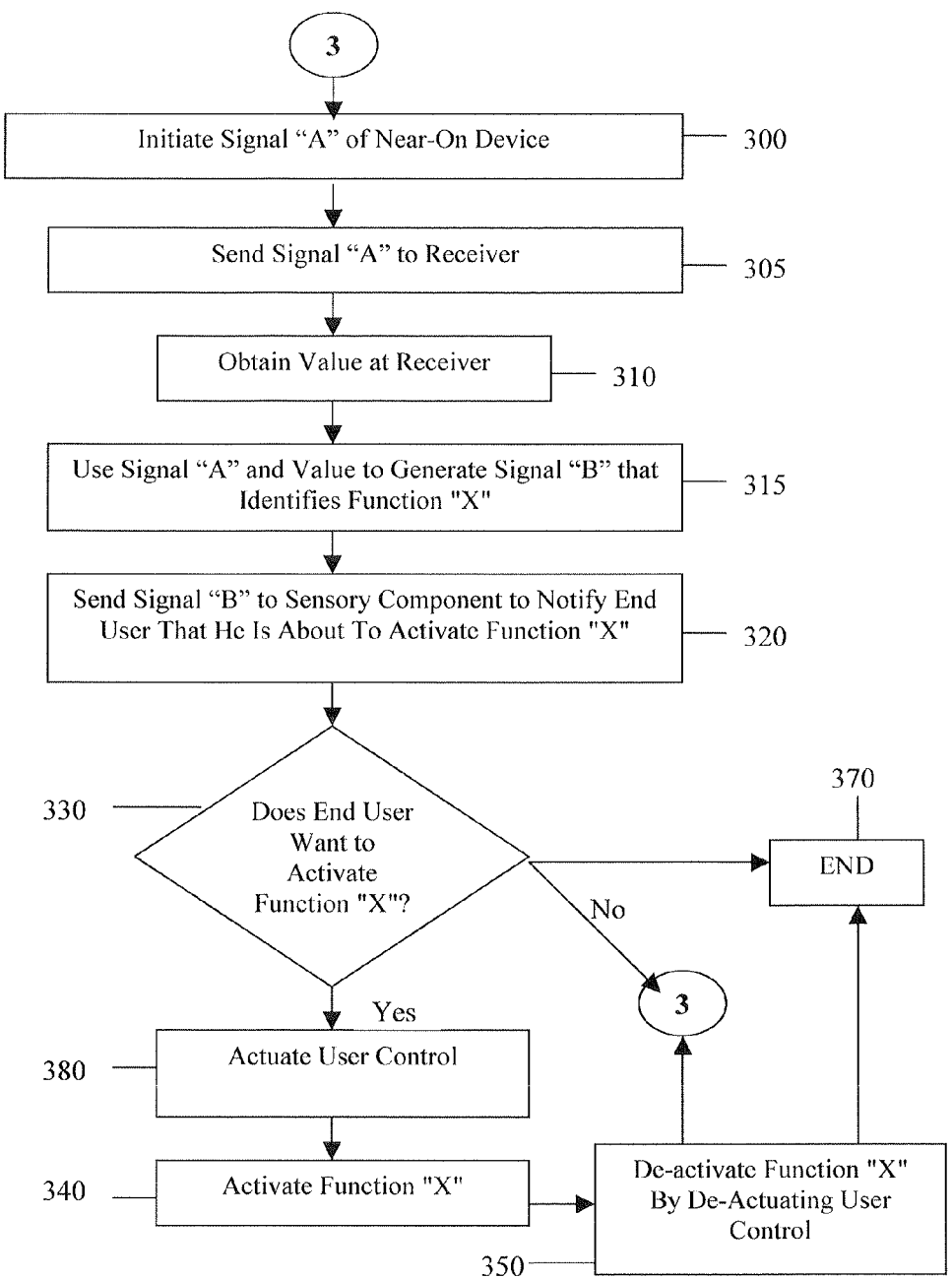
FIG. 3 is still another process flow of one or more embodiments of the present invention.
Figure 4A:
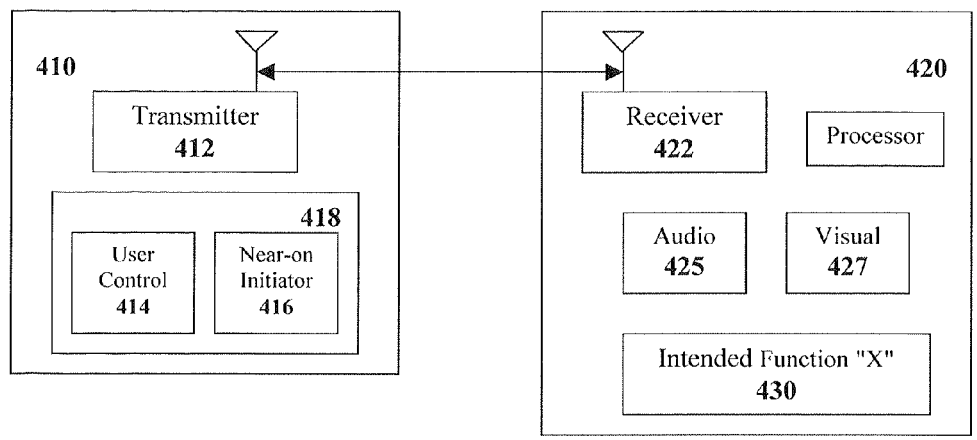
FIGS. 4A-B are diagrams illustrating systems and apparatus of one or more embodiments of the invention.
Figure 4B:
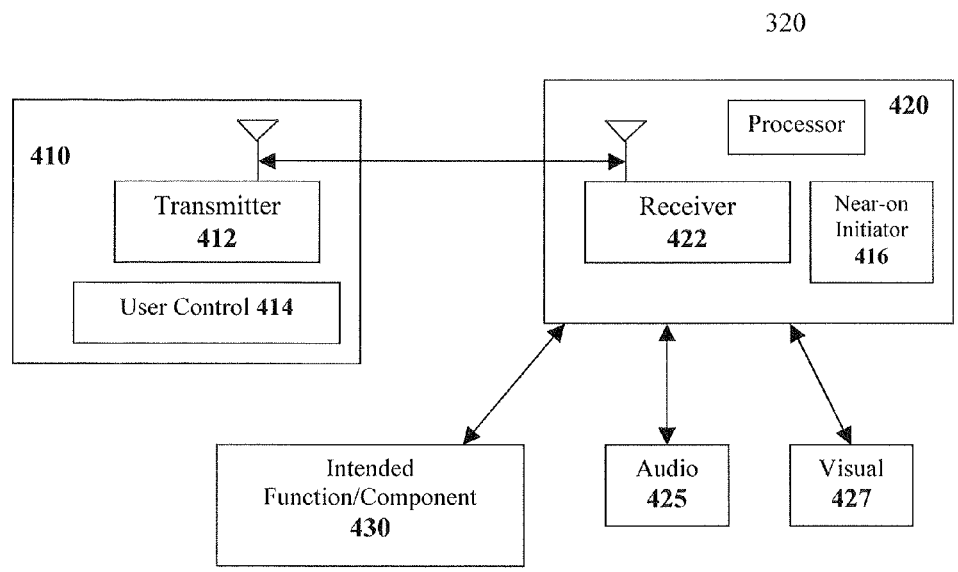

FIGS. 2 and 3 show different processes of the various alternate process flows envisioned and encompassed by the present invention. FIG. 2 is similar to the process flow of FIG. 1, however, this process provides for the near-on device 418 to be on or within an end-device that is the function "X" itself that is to be activated, or an end-device that has, contains or includes the function "X" or functions "X, Y, Z, AA . . . " that is/are to be activated (see, e.g., FIGS. 5A-C). Again, the near-on device 418 may be a near-on initiator 416 that is a single user control, or a near-on initiator first user control 416 in combination with an activating second user control 414. In this process flow, signal "A" is initiated upon actuating the near-on device 418 of the end-device at which point signal "A" is sent from the near-on device 418 to the receiver 422 of the end-device. The process flow of FIG. 2 then continues in accordance with the various embodiments of the invention as described above.

FIG. 3 shows another process flow of the invention whereby signal "A" is initiated prior to actuating the activating user control 414 of the near-on device 418. For instance, this process flow may be suitable for embodiments wherein a two-step actuation process takes place in the process flow (e.g., contact or apply at least partial pressure to near-on initiator 416, remove contact/pressure, and then contact or apply full pressure to actuate activating second user control 414). It also may be suitable in embodiments employing near-contact to actuate the near-on initiator 416 for initiating signal "A" (e.g., in embodiments implementing a near-on capacitive indicating membrane or layer over, in contact with or adjacent to a user control 414). Once signal "A" has been initiated, the process flow continues as in FIGS. 1 and 2 until step 380 at which point the activating user control is actuated (which may be a first actuation or contact step) for activating function "X" in step 340. It should be appreciated that many other process flows of the invention may be envisioned in accordance with the various descriptions of the invention.

Again, as discussed in relation to any and all of the various embodiments of the invention, this near-on technology may be attached to a device or fabricated in a form for use as a foot implemented control, a hand implemented control, a touch sensitive control, a voice activated control, a remotely activated control, a wire activated control, and the like. For ease of understanding the invention, and while not meant to be limiting, below are examples of various embodiments of the invention.

In one or more embodiments the invention is directed to wireless remote control of hand or foot actuated controls that are suitable for use in a variety of settings including, but not limited to, commercial, industrial, scientific, medical, residential and the like. A near-on device 418 of the invention is implemented on or in a first device 410 having a transmitter 412. As described in the various embodiments above, the near-on device 418 may be entirely linear in nature, entirely analog in nature or a combination of linear and analog in nature. For instance, the near-on device 418 may be implemented as human actuated device including, but not limited to, a hand device, foot device and the like, having switches, digital and/or linear hall devices, potentiometers, temperature probes, joysticks, and the like. The first device 410 may also include a plurality of the different embodiments of near-on devices 418 of the invention.

The transmitter 412 may be mounted inside, outside, or on an outside surface of the first device 410 and be adapted with infrared or radio frequency pairing to a receiver 422 that resides on a second device 420. For example, signals may be transmitted from the transmitter to the receiver at a radio frequency of about 2.4 ghz operating in the ISM band. The transmitter may be operated and maintained using batteries, whereby the life of these batteries is extended via hardware and software.

In one or more embodiments, the batteries may be primary alkaline batteries (i.e., those that are not re-chargeable.) These types of batteries are typically rated in Miliamp-hours from when the battery is new (1.5 volts) down to a terminal voltage of 0.9 volts. The number of cells required is dependent upon the lowest voltage required by any component on the transmitter. For instance, wherein the near-on device 418 includes a hall device as the near-on initiator 416, this hall device may require a minimum of 2.5 volts, such that, a 2.8 volt linear regulator may be chosen for implementation. The hall devices in this example preferably employ a sleep pin, which when held low, puts hall devices' outputs in a high impedance state allowing the outputs of several devices to be tied together. When a sleep pin is raised high its output is active and can be read by the analog to digital converter of the micro-processor. As such, each sleep pin can be raised sequentially and read by a single analog to digital input of the micro-processor. The sleep pins controls are also inputs to the analog to digital converter pins of the micro-processor. If a hall device is not used these pins can be used to read a potentiometer or other analog device. To further conserve the batteries, the power to the Hall devices, potentiometers etc. is applied by the micro-processor just prior to reading the device and doing an analog to digital conversion.

Once the near-on initiator 416 is actuated, signal "A" is generated and output from the transmitter 412. The transmitter 412 and the receiver 422 may each have an antenna, and communicate back and forth with each other using a synchronous frequency hopping transmission protocol. That is both signal "A" and signal "B" are sent via a frequency hoping protocol. The receiver 422 may reside in or on a second device 420. This second device 420 may also have or be in communication with (e.g., remote communication) an LCD screen (e.g., a touch screen color display) for visualizing the warning alert to the end-user and/or one or more speakers for sounding any alerts to the user (e.g., audio prompts), whereby these alerts relate to the device that is about to be activated or deactivated.

The receiver 422 may be adapted to be paired to the transmitter via infrared or RF. Further, the second device 420 having the receiver 422 may include relay outputs, linear outputs, and the like for transmitting signal "B" to the intended function 430 that is to be activated/deactivated. This intended function may include, for example, relay outputs, linear outputs, etc. The second device 420 having the receiver 422 may be mounted within a preexisting piece of equipment, or it may be its own independent and distinct device. Also, the second device may include software or logic that allows the system to operate at a desired linear range output (e.g., when a user wants 5V the system is programmed for 5V, etc.).

As other examples, various embodiments of the invention may be implemented in or with devices that have a number of controls in close proximity to one another. For example, devices having key pads may be provided with the present near-on technology. Devices suitable for use with the present invention having key pads include, but are not limited to, a phone (e.g., mobile or stationary phone), a smart phone, key board, MP3, video game (e.g., DS game), net-book, oven/stove, microwave, light fixture, or any other type of electronic component having a key pad for actuating a function thereon or associated with such component. Referring to FIGS. 5A-C, a device having a keypad (e.g., a cell phone) may be provided with a near-on initiator membrane or layer 416 (e.g., a capacitive layer or resistive layer) over a plurality of keypad user controls 414. Upon contact or near-contact with this membrane layer or regions a specific key is associate with the site of contact and this key pad is identified to the user either visually or auditorily. The end-user may then decide if this is in fact the desired key, and if so press or contact the membrane and underlying key. If it is not the desired key, the end user may contact or near-contact another site on the membrane layer or regions, and repeat this process until the desired key is obtained.

As still other examples, one or more embodiments of the invention may be used for identifying an item that can not be visually seen by the end-user. For instance, the near-on technology may be applied to caps, lids or tops on bottles to identify the type of bottle or item within such bottles. For instance, the bottle may be a pill bottle and the near-on technology may be used to send an auditory signal that identifies the contents in the bottle before such bottle is opened. It should be appreciated that numerous other applications exist to which the present embodiments of the invention may be applied and for which are encompassed by and within the descriptions of the present invention.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon. Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing. Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the end-user's computing device (such as, a computer), partly on the end-user's computing device, as a stand-alone software package, partly on the end-user's computing device and partly on a remote computing device or entirely on the remote computing device or server. In the latter scenario, the remote computing device may be connected to the end-user's computing device through any type of network, including a local area network (LAN) or a wide area network (WAN), or the connection may be made to an external computer (for example, through the Internet using an Internet Service Provider).

Aspects of the present invention are described above with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computing device (such as, a computer), special purpose computing device, or other programmable data processing apparatus to produce a machine, such that the instructions, which execute via the processor of the computing device or other programmable data processing apparatus, create means for implementing the functions/acts specified in the flowchart and/or block diagram block or blocks. These computer program instructions may also be stored in a computer readable medium that can direct a computing device, other programmable data processing apparatus, or other devices to function in a particular manner, such that the instructions stored in the computer readable medium produce an article of manufacture including instructions which implement the function/act specified in the flowchart and/or block diagram block or blocks. The computer program instructions may also be loaded onto a computer, other programmable data processing apparatus, or other devices to cause a series of operational steps to be performed on the computing device (such as, a computer), other programmable apparatus or other devices to produce a computer implemented process such that the instructions which execute on the computer or other programmable apparatus provide processes for implementing the functions/acts specified in the flowchart and/or block diagram block or blocks.

While the present invention has been particularly described, in conjunction with a specific preferred embodiment, it is evident that many alternatives, modifications and variations will be apparent to those skilled in the art in light of the foregoing description. It is therefore contemplated that the appended claims will embrace any such alternatives, modifications and variations as falling within the true scope and spirit of the present invention.

Thus, having described the invention, what is claimed is:

1. A method for function activation control of medical equipment comprising:
   providing a medical instrument having a desired function that performs a medical task;
   providing a foot-operated device in communication with the medical instrument, said foot-operated device controlling activation of said desired function of said medical instrument;
   an end-user temporarily actuating said foot-operated device by applying an initial pressure to said foot-operated device to generate a first signal including an identification of a function prior to activation of said function;
   transmitting said first signal to a second device that is separate and distinct from the foot-operated device, said second device receiving said first signal and determining said identification of said function prior to activation thereof;
   generating a second signal having said identification of said function at said second device;
   transmitting said second signal to a sensory component;
   said sensory component alerting said end-user of said identification of said function prior to activation thereof; and
   said end-user verifying that said identified function that is about to be activated is the desired function of said medical instrument prior to activation thereof, whereby,
      if said identified function is said desired function, then said end-user further actuating said foot-operated device by applying additional pressure to said foot-operated device to immediately activate said desired function and perform said medical task,
      if said identified function is not said desired function, then said end-user de-actuating said foot-operated device to prevent activation of said identified function.

2. The method of claim 1 wherein the foot-operated device comprises a foot-operated switch, a foot of the end-user applying the initial pressure to said foot-operated switch to generate the first signal whereby,
   if said identified function about to be activated is said desired function, then said foot of the end-user applying additional pressure down on the foot-operated switch to activate said desired function and perform said medical task,
   if said identified function is not said desired function, then removing said end-user's foot from contact with said foot-operated switch to prevent activation of said identified function.

3. The method of claim 1 wherein the foot-operated device comprises an electrically operated component selected from the group consisting of a mechanical switch, analog switch, electrical switch, limit switch, process switch, potentiometer, sensors, hall device and combinations thereof.

4. The method of claim 1 wherein the foot-operated device comprises a single user control.

5. The method of claim 1 wherein the foot-operated device comprises at least a two-part user control including a near-on initiator first user control in combination with an activating second user control, the near-on initiator first user control configured to be actuated before the activating second user control, whereby the near-on initiator first user control is actuating to generate the first signal, and if it is determined that said identified function is said desired function, said activating second user control is then actuated to activate said function.

6. The method of claim 1 wherein the foot-operated device is actuated by human contact, electrical contact, pressure, partial pressure, rotation, sound activation, remotely and combinations thereof.

7. The method of claim 1 wherein the sensory component is selected from the group consisting of a visual component, an auditory component and combinations thereof.

8. The method of claim 1 wherein the first signal further includes a unique identifier of said foot-operated device and state information corresponding to a state of actuation of said foot-operated device, said state of actuation of said foot-operated device correlating to whether or not said function has been activated.

9. The method of claim 8 wherein said state information is used to determine whether at least first and second predetermined threshold values have been met, said first threshold value comprising a start of a warning period at which the foot-operated device has been actuated, and the second threshold value comprising an end of the warning period at which the function has been activated.

10. A method for function activation control of medical equipment comprising:
    providing a medical device having a desired function that performs a medical task;
    providing a manually implemented foot-operated switch in communication the medical device, the manually implemented foot-operated switch controlling activation of said desired function of the medical device;

an end-user initially actuating said manually implemented foot-operated switch by applying an initial pressure to said foot-operated switch to generate a first signal including an identification of a function prior to activation of said function;

transmitting said first signal from the manually implemented foot-operated switch to a receiving device separate and distinct from the foot-operated switch through a remote wireless communication, said receiving device at least determining said identification of said function prior to activation thereof;

generating a second signal including said identification of said function at said receiving device;

transmitting said second signal to a sensory component;

said sensory component alerting said end-user of said identification of said function prior to activation thereof; and said end-user verifying that said identified function is the desired function of the medical device prior to activation of said function, whereby, if said identified function is said desired function, then said end-user further actuating said manually implemented foot-operated switch by applying additional pressure to said foot-operated switch to immediately activate said desired function and perform said medical task, if said identified function is not said desired function, then said end-user de-actuating said manually implemented foot-operated switch to prevent activation of said identified function.

11. The method of claim 10 wherein said function that is to be activated is associated with said medical device that performs a task in a field selected from the group consisting of medical, hospital, scientific, laboratory, commercial, industrial, manufacturing and residential.

12. A system for function activation control of medical equipment comprising:
a foot-operated device in communication with a medical device having a desired function that performs a medical task, said foot-operated device controlling activation of said function of said medical device;
a first signal generated by and wirelessly transmitted from said foot-operated device, the first signal including an identification of a function prior to activation of said function;
a separate and distinct second device receiving the first signal;
a set of instructions within said second device that determine said identification of said function prior to activation thereof;
a second signal generated by and transmitted from said second device;
a sensory component in communication with said second device, said sensory component receiving said second signal and alerting an end-user of said identification of said function prior to activation thereof for enabling determination of whether said identified function is the desired function of the medical device;
said foot-operated device having first and second pressure points, the first pressure point reached by applying an initial pressure to said foot-operated device at which said first signal is generated and the second pressure point reached by applying additional pressure to said foot-operated device at which said identified function is immediately activated.

13. A method for function activation control of a medical device comprising:
providing a first device in communication with a separate and distinct medical instrument having a desired medical function, the first device having a near-on initiator first user control and an activating second user control for controlling activation of said medical function;
an end-user partially actuating said first device by actuating the near-on initiator first user control to generate a first signal including an identification of a function prior to activation of said function;
transmitting said first signal to a separate and distinct second device, said second device receiving said first signal and determining said identification of said function prior to activation thereof;
generating a second signal having said identification of said function at said second device;
transmitting said second signal to a sensory component;
said sensory component alerting said end-user of said identification of said function prior to activation thereof; and
said end-user verifying that said identified function that is about to be activated is the desired medical function prior to activation thereof, whereby,
if said identified function is said desired function, then said end-user immediately and fully actuating said first device by actuating the activating second user control to immediately activate said desired medical function,
if said identified function is not said desired function, then said end-user de-actuating said first device to prevent activation of said function.

14. The method of claim 13 wherein the first device is a manually implemented device, the method further comprising:
the end-user initially applying partial pressure to said manually implemented device to generate the first signal;
transmitting said first signal to the second device for identification of said function;
said second device receiving said first signal and determining said identification of said function prior to activation thereof;
generating said second signal having said identification of said function at said second device;
transmitting said second signal to said sensory component;
alerting said end-user of said identification of said identified function prior to activation thereof, whereby,
if said identified function about to be activated is said desired function, then the end-user applying full pressure to the manually implemented device to immediately activate said function,
if said identified function is not said desired function, then the end-user ceasing applying pressure to said manually implemented device to prevent activation of said function.

15. The method of claim 14 wherein the manually implemented device comprises a foot-operated switch, a foot of the end-user applying the initial pressure to said foot-operated switch to generate the first signal whereby,
if said identified function about to be activated is said desired function, then said foot of the end-user applying additional pressure down on the foot-operated switch to immediately activate said function,
if said identified function is not said desired function, then removing said end-user's foot from contact with said foot-operated switch to prevent activation of said function.

* * * * *